United States Patent
Ross (10) Patent No.: US 10,213,525 B2
(45) Date of Patent: Feb. 26, 2019

(54) USE OF PERFUSION DECELLULARIZED LIVER FOR ISLET CELL RECELLULARIZATION

(71) Applicant: Miromatrix Medical Inc., Eden Prairie, MN (US)

(72) Inventor: Jeffrey Ross, Chaska, MN (US)

(73) Assignee: Micromatrix Medical, Inc., Eden Prairie, MN (US)

( * ) Notice: Subject to any disclaimer, the term of this patent is extended or adjusted under 35 U.S.C. 154(b) by 57 days.

(21) Appl. No.: 14/777,360

(22) PCT Filed: Mar. 13, 2014

(86) PCT No.: PCT/US2014/026363
§ 371 (c)(1),
(2) Date: Sep. 15, 2015

(87) PCT Pub. No.: WO2014/151739
PCT Pub. Date: Sep. 25, 2014

(65) Prior Publication Data
US 2016/0030638 A1 Feb. 4, 2016

Related U.S. Application Data

(60) Provisional application No. 61/789,927, filed on Mar. 15, 2013.

(51) Int. Cl.
| | | |
|---|---|---|
| C12N 5/00 | (2006.01) | |
| A61L 27/38 | (2006.01) | |
| C12N 5/071 | (2010.01) | |
| A61L 27/36 | (2006.01) | |
| A61L 27/40 | (2006.01) | |
| A61L 27/54 | (2006.01) | |
| A61L 27/58 | (2006.01) | |

(52) U.S. Cl.
CPC ....... *A61L 27/3834* (2013.01); *A61L 27/3633* (2013.01); *A61L 27/3683* (2013.01); *A61L 27/40* (2013.01); *A61L 27/54* (2013.01); *A61L 27/58* (2013.01); *C12N 5/069* (2013.01); *C12N 5/0671* (2013.01); *C12N 5/0676* (2013.01); *C12N 5/0678* (2013.01); *C12N 5/0697* (2013.01); *C12N 2501/115* (2013.01); *C12N 2501/999* (2013.01); *C12N 2502/28* (2013.01)

(58) Field of Classification Search
CPC .................................................. C12N 5/0062
See application file for complete search history.

(56) References Cited

U.S. PATENT DOCUMENTS

2013/0156744 A1* 6/2013 Taylor ................ A61L 27/3604
424/93.7

FOREIGN PATENT DOCUMENTS

| HK | 1218929 A1 | 3/2017 |
|---|---|---|
| WO | WO-2007025233 A1 | 3/2007 |
| WO | WO-2010120539 A2 | 10/2010 |
| WO | WO-2011002926 A2 | 1/2011 |
| WO | WO-2012005760 A1 | 1/2012 |
| WO | WO-2012031162 A1 | 3/2012 |
| WO | WO-2014151739 A1 | 9/2014 |

OTHER PUBLICATIONS

"European Application Serial No. 14721618.8, Response filed Jul. 11, 2017 to Communication Pursuant to Article 94(3) EPC dated Jan. 2, 2017", 15 pgs.
"Singapore Application Serial No. 11201507620V, Response filed Jun. 29, 2017 to Office Action dated Feb. 15, 2017", 26 pgs.
Baneriee, Ipsita, et al., "Impact of co-culture on pancreatic differentiation of embryonic stem cells", J. Tissue Eng. Regen. Med., 5(4), (2011), 313-323.
Cechin, S., et al., "Influence of In Vitro and In Vivo Oxygen Modulation on β Cell Differentiation From Human Embryonic Stem Cells.", Stem Cells Transl. Med., 3(3), (2014), 277-289.
Gualandris, A., et al., "The Latent Transforming Growth Factor-β-binding Protein-1 Promotes In Vitro Differentiation of Embryonic Stem Cells into Endothelium", Mol. Biol. Cell., 11(12), (2000), 4295-4308.
Hirashima, M., et al., "Maturation of Embryonic Stem Cells Into Endothelial Cells in an in Vtro Model of Vasculogenesis.", Blood, 93(4), (1999), 1253-1263.
Lamb, M., et al., "In Vitro Maturation of Viable Islets From Partially Digested Young Pig Pancreas", Cell Transplant., 23(3), (2014), 263-272.
Margariti, A., et al., "Direct reprogramming of fibroblasts into endothelial cells capable of angiogenesis and reendothelialization in tissue-engineered vessles", Proc. Natl. Acad. Sci. USA, 109(34), (2012), 13793-137938.
Saito, Hiroki, et al., "Generation of Glucose-Responsive Functional Islets with a Three-Dimensional Structure from Mouse Fetal Pancreatic Cells and iPS Cells In Vitro", PLoS ONE, 6(12): e28209, (Dec. 2011), 1-7.
Schenke-Lavland, K., et al., "Reprogrammed Mouse Fibroblasts Differentiate into Cells of the Cardiovascular and Hematopoietic Lineages", Stem Cells, 26(6), (2008), 1537-1546.
Shen, Gan, et al., "Tissue engineering of blood vessels with endothelial cells differentiated from mouse embryonic stem cells", Cell Research, 13(5), (2003), 335-341.
Shirakigawa, N., et al., "Decellularized liver as a practical scaffold with a vascular network template for liver tissue engineering", (Abstract Only), J Biosci Bioeng., 114(5), 546-551, (2012), 1 pg.
Smardencas, A., et al., "Seeding of endothelial cells on the luminal surface of a sheet model of cold-stored (at 4° C.) sheep carotid arteries.", Cell Transplant., 21(I), (2012), 285-297.
Tateishi, Keisuke, et al., "Generation of insulin-secreting islet-like clusters from human skin fibroblasts", J Biol Chem., 283(46), (Nov. 14, 2008), 31601-31607.

(Continued)

*Primary Examiner* — Ruth A Davis
(74) *Attorney, Agent, or Firm* — Wilson Sonsini Goodrich & Rosati (57) ABSTRACT

The invention provides a method for preparing a perfusion based islet cell containing extracellular matrix of liver, an islet cell recellularized extracellular matrix, and methods of using the recellularized matrix.

24 Claims, 5 Drawing Sheets

(56) References Cited

OTHER PUBLICATIONS

Thebaud, N. B., et al., "Human progenitor-derived endothelial cells vs. venous endothelial cells for vascular tissue engineering: an in vitro study.", J Tissue Eng Regen Med., 4(6), (2010), 473-484.
"European Application Serial No. 14721618.8, Offfice Action dated Nov. 20, 2015", 2 pgs.
"European Application Serial No. 14721618.8, Response filed May 26, 2016 to Office Action dated Nov. 20, 2015", 8 pgs.
"International Application Serial No. PCT/US2014/026363, International Preliminary Report on Patentability dated Sep. 24, 2015", 12 pgs.
"Singapore Application Serial No. 11201507620V, Office Action dated May 9, 2016", Written Opinion, 7 pgs.
Badylak, Stephen F, et al., "Marrow-Derived Cells Populate Scaffolds Composed of Xenogeneic Extracellular Matrix", *Experimental Hematology*, 29(11), (Nov. 2001), 1310-1318.
"International Application Serial No. PCT/US2014/026363, International Search Report dated Jul. 15, 2014", 4 pgs.
"International Application Serial No. PCT/US2014/026363, Written Opinion dated Jul. 15, 2014", 6 pgs.
Badylak, S. F., et al., "Whole-organ tissue engineering: decellularization and recellularization of three-dimensional matrix scaffolds", Annu Rev Biomed Eng., 13, (Aug. 15, 2011), 27-53.
Barakat, O., et al., "Use of Decellularized Porcine Liver for Engineering Humanized Liver Organ", Journal of Surgical Research, 173(1), (2012), e11-e25.
Song, Jeremy J, et al., "Organ engineering based on decellularized matrix scaffolds", Trends in Molecular Medicine, vol. 17, No. 8, (Aug. 2011), 424-432.

Uygun, B. E, et al., "Decellularization and recellularization of whole livers", J Vis Exp., (48), (Abstract Only), (Feb. 2011), 1 pg.
Uygun, Basak E, et al., "Organ reengineering through development of a transplantable recellularized liver graft using decellularized liver matrix", Nature Medicine, vol. 16, No. 7, (2010), 814-820.
"European Application Serial No. 14721618.8, Communication Pursuant to Article 94(3) EPC dated Jan. 2, 2017", 4 pgs.
"Singapore Application Serial No. 11201507620V, Office Action dated Feb. 13, 2017", 14 pgs.
De Carlo, E, et al., "Pancreatic Acellular Matrix Supports Islet Survival and Function in a Synthetic Tubular Device: In Vitro and in Vivo Studies", International Journal of Molecular Medicine, vol. 25, No. 2,, (Feb. 2010), 195-202.
Abbott, A. Cell culture: biology's new dimension. Nature. Aug. 21, 2003;424(6951):870-2.
Cukierman, et al. Taking cell-matrix adhesions to the third dimension. Science. Nov. 23, 2001;294(5547):1708-12.
D'Amour, et al. Production of pancreatic hormone-expressing endocrine cells from human embryonic stem cells. Nat Biotechnol. Nov. 2006;24(11):1392-401.
Den Butter et al. Comparison of solutions for preservation of the rabbit liver as tested by isolated perfusion. Transpl. Int 8, (466-471), 1995.
Firth et al. Sodium handling in the isolated perfused kidney of the cirrhotic rat. Clinical Science 77.6 (1989): 657-661.
Mazzetti et al. Molecular anatomy of the cerebral microvessels in the isolated guinea-pig brain. Brain Research 999, (2004), 81-90.
Van Putte, et al. Single-pass isolated lung perfusion versus recirculating isolated lung perfusion with melphalan in a rat model. Ann Thorac Surg. Sep. 2002;74(3):893-8; discussion 898.
Wagner et al. The isolated normothermic hemoperfused porcine forelimb as a test system for transdermal absorption studies J Artif. Organs 6(3), (2003), 183-191.

\* cited by examiner

USE OF PERFUSION DECELLULARIZED LIVER FOR ISLET CELL RECELLULARIZATION

CROSS-REFERENCE TO RELATED APPLICATIONS

This application is a U.S. National Stage Filing under 35 U.S.C. 371 from International Application No. PCT/US2014/026363, filed on 13 Mar. 2014 and published as WO 2014/151739 on 25 Sep. 2014, which application claims the benefit of the filing date of U.S. application Ser. No. 61/789,927, filed on Mar. 15, 2013, the disclosures of which are incorporated by reference herein.

BACKGROUND

Tissue engineering is a rapidly growing field that seeks to repair or regenerate damaged or diseased tissues and organs through the implantation of combinations of cells, scaffolds and soluble mediators. Current stem cell differentiation and primary cell culture is generally achieved under 2-dimensional (2D) culture conditions. That system allows for the expansion of specific cell populations but is limited in its ability retain functional cellular phenotypes, to support high density cell culture and long term primary or differentiated cell function. For example, in contrast to the limited availability of large numbers of primary cells needed for certain cellular therapies, the number of stem cells can be greatly expanded while retaining the ability to differentiate into specific lineages. The control of stem cell fate (e.g., differentiation), either in vivo or in vitro, has been attributed principally to genetic and molecular mediators (e.g., growth factors and transcription factors). Although stem and progenitor cell differentiation can result in cells with appropriate lineage- or tissue-specific gene expression, the differentiated cells can lack functional properties needed for in vitro or in vivo applications.

SUMMARY OF THE INVENTION

The invention provides a method to prepare a graft comprising a recellularized extracellular matrix of a mammalian liver, liver lobe or portion thereof. In one embodiment, the portion is a total inflated volume of greater than or equal to about 15 cm$^3$. The method includes selecting a perfusion decellularized extracellular matrix of a mammalian liver, a liver lobe or a portion thereof and two populations of cells. The first population of mammalian cells includes endothelial cells or stem or progenitor cells capable of differentiation into endothelial cells, and the second population of mammalian cells includes islet cells, beta cells, insulin like cells, or stem cells or progenitor cells capable of differentiation into islet cells or beta cells. The perfusion decellularized extracellular matrix and the two population of cells are contacted under conditions and for a period of time that provide for re-endothelialization of the vasculature of the perfusion decellularized extracellular matrix, and recellularization of the perfusion decellularized extracellular matrix with the islet cells, beta cells or insulin like cells or recellularization and differentiation and functional maturation of the stem or progenitor cells into islet cells, beta cells or insulin like cells in the perfusion decellularized extracellular matrix. In one embodiment, the cells in the first and the second populations are xenogeneic to the decellularized extracellular matrix. In one embodiment, the cells in the first and the second populations are allogeneic to the decellularized extracellular matrix. In one embodiment, the cells in the first population, the second population, or both, include iPS cells. In one embodiment, the into islet cells, beta cells or insulin like cells are encapsulated In one embodiment, the cells in the first population, the second population, or both, are primary cells. In one embodiment, the cells in the first population, the second population, or both, are embryonic stem cells. In one embodiment, the first population, the second population, or both, comprise a plurality of different cell types. In one embodiment, the perfusion decellularized extracellular matrix contains an intact vascular extracellular matrix network. In one embodiment, the first population of cells is contacted with the extracellular matrix either by injection or perfusion, or a combination thereof. In one embodiment, the second population of cells is contacted with the extracellular matrix either by injection or perfusion, or a combination thereof.

In one embodiment, the method includes implanting the extracellular matrix in a mammal. In one embodiment, the extracellular matrix is implanted in the mammal prior to contact with the first population, the second population, or both. In one embodiment, the extracellular matrix is implanted in a mammal after contact with the first population, but before the second population. In one embodiment, the extracellular matrix is implanted in a mammal after contact with the second population but before contact with the first population. In one embodiment, the extracellular matrix is implanted in a mammal after contact with the first population and the second population.

Further provided is a method to enhance insulin control in a mammal that lacks or has reduced insulin control. The method includes providing a re-endothelialized extracellular matrix of a mammalian liver, a liver lobe or a portion thereof having a population of mammalian cells including islet cells, beta cells, islet like cells, or stem cells or progenitor cells capable of differentiation into islet cells or beta cells. The re-endothelialized matrix may be prepared by introducing mammalian endothelial cells or cells capable of differentiation into mammalian endothelial cells and the population to a decellularized extracellular matrix of the mammalian liver, liver lobe or portion thereof. The re-endothelialized matrix having the population of cells including islet cells, beta cells, islet like cells or stem cells or progenitor cells capable of differentiation into islet or beta cells, is introduced to a mammal that lacks or has reduced insulin control so as to provide for control of blood glucose in the mammal.

Also provided is a method to enhance insulin control in a mammal that lacks or has reduced insulin control. The method includes providing a re-endothelialized extracellular matrix of a mammalian liver, a liver lobe or a portion thereof prepared by introducing mammalian endothelial cells or cells capable of differentiation into mammalian endothelial cells, to a decellularized extracellular matrix of mammalian liver, liver lobe or portion thereof. The re-endothelialized matrix is introduced to a mammal that lacks or has reduced insulin control and a population of cells is introduced to the mammal, including islet cells, beta cells, islet like cells or stem cells or progenitor cells capable of differentiation into islet or beta cells, in an amount effective to provide for control of blood glucose in the mammal.

The invention further provides a method to enhance insulin control in a mammal that lacks or has reduced insulin control. The method includes providing a mammal that lacks or has reduced insulin control and has an implanted re-endothelialized matrix of a mammalian liver, a liver lobe or a portion thereof. The re-endothelialized matrix may be prepared by introducing mammalian endothelial cells to a decellularized extracellular matrix of a mammalian liver, liver lobe or portion thereof. A population of cells is introduced to the mammal including islet cells, beta cells, islet like cells, or stem cells or progenitor cells capable of differentiation into islet cells, in an amount effective to provide for control of blood glucose in the mammal. The population of cells can be encapsulated in materials and methods known to those in the art.

DETAILED DESCRIPTION OF THE INVENTION

The present invention provides for engineering of cells and ECMs that, through physical as well as molecular interactions, direct control of cell behavior by controlling the environment of those cells. In particular, the present invention provides engineered organs and tissues having perfusion decellularized liver ECM implanted with a population of cells, including combinations of cells, and subjected to culture conditions, e.g., including perfusion of soluble mediators, which ECM structure and culture conditions result in functional cells. In particular, the invention provides for the growth and functional maintenance of primary cells including fetal derived cells, e.g., organ-specific cells obtained from fetal cells or neonate cells (for instance, cells that are committed to a specific lineage but are not terminally differentiated). In contrast to the use of in vivo transplantation to differentiation for hES cells into insulin producing cells, the present invention provides for the use of liver ECM to provide a structure for insulin producing cells or to achieve differentiation to functional beta cells capable of insulin regulation in response to glucose stimulation. In one embodiment, the differentiated cells of the invention have at least 20% of the function of corresponding normal cells in vivo.

The invention provides perfusion decellularized liver, liver lobe or portion thereof extracellular matrix (ECM) and systems useful to support islet cells, beta cells or islet like cells maintenance, or differentiation and/or maturation of stem or progenitor cells, to islet cells, beta cells or insulin like cells, or any combination thereof, in the matrices. Primary cells are cells obtained from an organism that may then be cultured in vitro, although those cells do not proliferate indefinitely. Differentiated cells include primary cells and cells that have been differentiated in vitro, e.g., stem cells or progenitor cells, in a perfusion decellularized matrix of the invention. In one embodiment, at least 5%, 10% or 20%, or more, of the differentiated cells have a functionally mature phenotype. A tissue is a group of cells with a common structure and function, e.g., epithelial tissue, connective tissue, muscle tissue (skeletal, cardiac, or smooth muscle), and nervous tissue, and includes a pliable sheet that covers or lines or connects organs. An organ is a collection of tissues (two or more) joined in structural unit to serve a common function. As used herein, a portion of a liver, a liver lobe and liver include vascularized structures.

In one embodiment, the present invention provides for the use of a 3D liver derived ECM scaffold for islet cell, beta cell, islet like cell, stem cell, and/or progenitor cell maintenance, and for stem cell and progenitor cell types, differentiation and/or maturation into islet cells, beta cell or islet like cells. Differentiation is a process by which cells acquire a new phenotype that is distinct from the original cell population, e.g., distinct cellular gene and/or protein expression and/or function(s). Maturation further clarifies the phenotype of the cell population as having the normal mature functional capacity of a cell in an in vivo cell population. In one embodiment, the scaffold is a perfusion decellularized ECM liver lobe, e.g., a portion of a liver ECM. In another embodiment, the scaffold is a perfusion decellularized ECM liver. Such scaffolds may be employed to engineer delivery systems for heterologous cell types for therapy.

Perfusion decellularized ECM from organs or tissues such as liver or liver lobes retains more of the native microstructure, including an intact vascular and/or microvascular system, compared to other decellularization techniques such as immersion based decellularization. For example, perfusion decellularized ECM from liver or liver lobes preserves the collagen content and other binding and signaling factors and vasculature structure, thus providing for an environment for re-endothelialization of introduced cells. In one embodiment, perfusion decellularized ECM from liver, liver lobe or a portion thereof is perfused with endothelial cells in media using the vasculature of the perfusion decellularized ECM under appropriate conditions, including appropriate pressure and flow to mimic the conditions normally found in the organism. The normal pressures of human sized organs is between about 20 to about 200 mm Hg with the resulting flow rate dependent upon the incoming perfusion vessel diameter.

In one embodiment, the invention provides a method to prepare an organ—or tissue graft from a perfusion decellularized matrix and cells, e.g., cells that differentiate into specific functional cell types. The method includes selecting a perfusion decellularized matrix of an organ or tissue, e.g., from a non-human mammal, and populations of cells, e.g., xenogeneic or allogenic cells including progenitor cells capable of differentiation to cell types present in a native organ or tissue. The selected perfusion decellularized matrix is contacted with the population(s) of cells which may include progenitor cells under conditions and for a period of time that provide for recellularization of the perfusion decellularized matrix and differentiation of cells in the population into functional cells.

In one embodiment, the invention provides a method to prepare a islet cell containing delivery system having perfusion decellularized matrix of a liver, liver lobe or portion thereof and islet cells, beta cells or islet like cells, or cells that differentiate into islet cells, beta cells or islet like cells. The perfusion decellularized matrix is contacted with a population of endothelial cells and cells that include islet cells, beta cells, islet like cells, progenitor cells and/or stem cells under conditions and for a period of time that provide for re-endothelialization and functioning of islet cells in the matrix. In one embodiment, the stem cells are induced pluipotent stem (iPS) cells. In one embodiment, the stem cells are embryonic stem (ES) cells, e.g., human ES cells. In one embodiment, the stem cells are adult stem cells.

In one embodiment, a portion of a liver or liver lobe ECM is employed in the methods of the invention. In one embodiment, the portion is about 5 to about 10 mm in thickness. In one embodiment, the portion is about 70 to about 100 mm in thickness.

In one embodiment, stem or progenitor cells are seeded onto a perfusion decellularized liver ECM scaffold and cultured for a time and under conditions that result in re-endothelialization. In one embodiment, endothelial cells are seeded onto a perfusion decellularized liver ECM scaffold for a time and under conditions that result in re-endothelialization. In another embodiment, partially differentiated pancreatic cells derived from ES or iPS cells are seeded onto a perfusion decellularized liver ECM scaffold and cultured for a time and under conditions that result in fully functional alpha cells, PP cells, delta cells, epsilon cells, and/or beta cells, e.g., where alpha cells produce glucagon, beta cells produce insulin and amylin, delta cells produce somatostatin, PP cells produce pancreatic polypeptide, epsilon cells produce ghrelin. In another embodiment, differentiated pancreatic cells are seeded onto a perfusion decellularized liver ECM scaffold for a time and under conditions that result in fully functional alpha cells, PP cells, delta cells, epsilon cells, and/or beta cells, e.g., where alpha cells produce glucagon, beta cells produce insulin and amylin, delta cells produce somatostatin, PP cells produce pancreatic polypeptide, epsilon cells produce ghrelin. In one embodiment, the culturing results in greater than 35% of the cells expressing insulin in response to glucose stimulation. In another embodiment, islet cells, beta cells or insulin like cells are encapsulated in alginate prior to delivery to the re-endothelialized liver graft.

Perfusion decellularized matrices of organs with a substantially closed vascular system are particularly useful because perfusion decellularization preserves the intact matrix and microenvironment, including an intact vascular and microvascular system, that vascular system may be utilized to deliver cells as well as nutrients and/or differentiation or maintenance factors, to the cells in vitro. A "substantially closed" vasculature system with respect to an organ means that, upon perfusion with a liquid, the majority of the liquid is contained within the solid organ and does not leak out of the solid organ, assuming the major vessels are cannulated, ligated, or otherwise restricted. Despite having a "substantially closed" vasculature system, the organs have defined "entrance" and "exit" vessels which are useful for introducing and moving the liquid throughout the organ during perfusion. Cells and nutrients and/or other factors may be delivered by other means, e.g., injection, or passive means, or a combination thereof. In one embodiment, a cell population of interest is perfused into the perfusion decellularized organ ECM allowing for the seeding into the interstitial space or matrix outside of the vascular conduits. This includes the active migration and/or homing of cells to their native microstructure, e.g. the homing of endothelial cells to the vasculature. In one embodiment, an endothelial cell population is perfused into the perfusion decellularized ECM liver, liver lobe or portion thereof followed by a second cell population, e.g., beta cell population, where the endothelial cells remain in the vascular conduits as in their native microenvironment. In another embodiment, two or more cell populations are combined and perfused together. In another embodiment, two or more distinct cell populations are introduced serially through either perfusion, direct injection or a combination of both. For example, islet cells or islet like cells may be introduced to a perfusion decellularized liver matrix either through perfusion or injection followed by the seeding of endothelial cells. In another embodiment, perfusion decellularized liver matrix is seeded with fetal endothelial cells. In another embodiment, endothelial cells are seeded in the matrix followed by islet cells.

The cells may be introduced in media that support the proliferation, metabolism, and/or differentiation of the cells. Alternatively, after the cells have populated the ECM, the medium is changed to one that supports the proliferation, metabolism and differentiation of the cells. The cultured cells may exist in the ECM at physiological cell densities and, in the presence of media that support the proliferation, metabolism, and/or differentiation of the cells and/or the appropriate microenvironment in the ECM, allow for the maintenance and/or functional differentiation of the cells.

In one embodiment, partially differentiated beta cells cultured on a perfusion decellularized liver matrix result in cells capable of insulin regulation and release in respect to various glucose or electrical triggers.

The cells and ECM may be xenogeneic or allogeneic. In one embodiment, partially or completely differentiated human cells and a perfusion decellularized organ or tissue from a small animal, e.g., a nonhuman mammal such as an immature pig, can be combined. In one example, a perfusion decellularized liver matrix from a human or pig is seeded with partially differentiated human ES derived islet cells providing allogeneic or xenogeneic, respectively, cell seeded matrices. In one embodiment, differentiated beta cells in the matrix release insulin in response to glucose stimulation. In one embodiment, the cells and the perfusion decellularized organ or tissue are allogeneic. In one embodiment, the cells and the perfusion decellularized matrix are xenogeneic. In one embodiment, the two populations of cells, e.g., endothelial cells and islet cells, are from the same organism. In one embodiment, the two populations of cells, e.g., endothelial cells and islet cells, are allogeneic. In one embodiment, the two populations of cells, e.g., endothelial cells and islet cells, are xenogeneic. In one embodiment, the cells in the matrix include human cells and the perfusion decellularized matrix is from a nonhuman mammal.

In one embodiment, the invention provides a method to provide mature cells in vitro. The method includes providing a recellularized matrix of the invention; and allowing for differentiation or maturation of the cells in the matrix. In one embodiment, the matrix is from a porcine, bovine, equine, canine, feline, caprine, non-human primate or human liver, liver lobe or portion thereof. In one embodiment, the cells in the matrix are functional functional beta-cells. In one embodiment, differentiated beta cells in the matrix release insulin in response to glucose stimulation. In one embodiment, the cells and the perfusion decellularized organ or tissue are allogeneic. In one embodiment, the cells and the perfusion decellularized matrix are xenogeneic. In one embodiment, the cells in the matrix include human hepatocytes and the perfusion decellularized matrix is from a nonhuman mammal.

Perfusion Decellularized ECM

Studies have shown that connective tissue cells behave very differently in 3D as opposed to 2D cultures (Cukierman et al., *Science,* 294:1708 (2001)). For example, culture of fibroblasts on flat substrates induces a polarity that does not occur in vivo. Further, when fibroblasts and other cell types are cultured in 3D tissue-derived matrices, they develop mature integrin-containing focal adhesion complexes within minutes that resemble the complexes found in vivo, whereas only primitive adhesion complexes develop in 2D cultures or even simple 3D type I collagen gels or Matrigel. These adhesion complexes are required for appropriate growth factor-activated receptor signaling and rapid (within 5 minutes) initiation of synthesis of their own ECM components and factors that alter the ECM (Cukierman et al., 2001; Abbott, *Nature*, 424:870 (2003)). In addition, cells in ECM culture deposit autocrine growth factors into tissue-derived matrices, a process that may be required for appropriate presentation of the growth factor to target cells. Such factors are mainly secreted into the culture medium in 2D cultures.

As mentioned above, physical interactions with the ECM, in addition to chemical, molecular (e.g., soluble mediators), or genetic (cell-type) factors, may regulate cell fate. For example, ECM-based control of the cell may occur through multiple physical mechanisms, such as ECM geometry at the micro- and nanoscale, ECM elasticity, or mechanical signals transmitted from the ECM to the cells.

The invention includes the use of engineered perfusion decellularized liver ECMs that allow for a highly vascularized structure to support islet cells, beta cells or islet like cells, e.g., from adult or embryonic stem cells. The perfusion decellularized matrices of the invention mimic the intricate and highly ordered nature of native ECM vasculature and the likely reciprocal interaction between cells and the ECM. In particular, the ECM may provide vascular-specific cues to stem or progenitor cells. In particular, distinct matrix proteins may be important for the specificity of ECM via their contribution to the architecture of the ECM or via their ability to interact with growth factors and/or the resident cells themselves.

Perfusion decellularization of tissue or organ ECM provides an intact ECM that has the ability to provide the structural, biochemical, and mechanical properties to enable functional cell differentiation and maintenance. Thus, perfusion decellularization of organs allows organs to serve as a tissue/organ specific bioreactor for stem or progenitor cell differentiation. Moreover, perfusion decellularization of organ or tissue ECM is superior to immersion in terms of preserving an intact matrix with structural and biochemical cues, including intact vasculature. In addition, perfusion decellularization provides advantages relative to immersion decellularization when tissue or organ thickness exceeds about 2 mm in thickness.

Decellularization of Organs or Tissues

Decellularization generally includes the following steps: stabilization of the solid organ, e.g., a vascuarlized structure thereof, or tissue, decellularization of the solid organ or tissue, renaturation and/or neutralization of the solid organ or tissue, washing the solid organ, degradation of any DNA remaining on the organ, disinfection of the organ or tissue and homeostasis of the organ.

The initial step in decellularizing an organ vascularized structure or tissue is to cannulate the organ or tissue. The vessels, ducts, and/or cavities of an organ or tissue tissue may be cannulated using methods and materials known in the art. Next, the cannulated organ vascuarlized structure or tissue is perfused with a cellular disruption medium. Perfusion through an organ can be multi-directional (e.g., antegrade and retrograde).

Langendorff perfusion of a heart is routine in the art, as is physiological perfusion (also known as four chamber working mode perfusion). See, for example, Dehnert, The Isolated Perfused Warm-Blooded Heart According to Langendorff, In Methods in Experimental Physiology and Pharmacology: Biological Measurement Techniques V. Biomesstechnik-Verlag March GmbH, West Germany, 1988.

Briefly, for Langendorff perfusion, the aorta is cannulated and attached to a reservoir containing physiological solution to allow the heart to function outside of the body for a specified duration of time. To achieve perfusion decellularization the protocol has been modified to perfuse a cellular disruption medium delivered in a retrograde direction down the aorta either at a constant flow rate delivered, for example, by an infusion or roller pump or by a constant hydrostatic pressure pump. In both instances, the aortic valves are forced shut and the perfusion fluid is directed into the coronary ostia (thereby perfusing, via antegrade, the entire ventricular mass of the heart), which then drains into the right atrium via the coronary sinus. For working mode perfusion, a second cannula is connected to the left atrium and perfusion can be changed to retrograde.

In one embodiment, a physiological solution includes phosphate buffer saline (PBS). In one embodiment, the physiological solution is a physiologically compatible buffer supplemented with, e.g., nutritional supplements (for instance, glucose). For liver, the physiological solution may be Krebs-Henseleit buffer having 118 mM NaCl, 4.7 mM KCl, 1.2 mM $MgSO_4$, 1.2 mM $KH_2PO_4$, 26 mM $NaHCO_3$, 8 mM glucose, and 1.25 mM $CaCl_2$ supplemented with 2% BSA. For re-endothelialized liver grafts with islet, beta-cells or insulin like cells, the phyciological solution may be Miami modified media-1 supplemented with or without prolactin or modified CMRL 1066 tissue culture media containing: 10% fetal bovine serum, 25 mM HEPES, 100 units/ml penicillin, and 100 μg/ml streptomycin, pH 7.4 with or without VEGF.

Methods are known in the art for perfusing other organ or tissues. By way of example, the following references describe the perfusion of lung, liver, kidney, brain, and limbs. Van Putte et al., *Ann. Thorac. Surg.*, 74(3):893 (2002); den Butter et al., *Transpl. Int.*, 8:466 (1995); Firth et al., *Clin. Sci. (Lond.)*, 77(6):657 (1989); Mazzetti et al., *Brain Res.*, 999(1):81 (2004); Wagner et al., *J. Artif. Organs*, 6(3):183 (2003).

One or more cellular disruption media may be used to decellularize an organ or tissue. A cellular disruption medium generally includes at least one detergent such as but not limited to SDS, PEG, CHAPS or Triton X. A cellular disruption medium can include water such that the medium is osmotically incompatible with the cells. Alternatively, a cellular disruption medium can include a buffer (e.g., PBS) for osmotic compatibility with the cells. Cellular disruption media also may include enzymes such as, without limitation, one or more collagenases, one or more dispases, one or more DNases, or a protease such as trypsin. In some instances, cellular disruption media also or alternatively may include inhibitors of one or more enzymes (e.g., protease inhibitors, nuclease inhibitors, and/or collegenase inhibitors).

In certain embodiments, a cannulated organ or tissue may be perfused sequentially with two different cellular disruption media. For example, the first cellular disruption medium may include an anionic detergent such as SDS and the second cellular disruption medium can include an ionic detergent such as Triton X. Following perfusion with at least one cellular disruption medium, a cannulated organ or tissue may be perfused, for example, with wash solutions and/or solutions containing one or more enzymes such as those disclosed herein.

Alternating the direction of perfusion (e.g., antegrade and retrograde) may assist in decellularizing the entire organ or tissue. Decellularization generally decellularizes the organ from the inside out, resulting in very little damage to the ECM. An organ or tissue may be decellularized at a suitable temperature between 4 and 40° C. Depending upon the size and weight of an organ or tissue and the particular detergent(s) and concentration of detergent(s) in the cellular disruption medium, an organ or tissue generally is perfused from about 0.05 hours to about 5 hours, per gram of solid organ or tissue (generally >50 grams), or about 2 hours to about 12 hours, per gram of solid organ or tissue for organs (generally <50 grams), with cellular disruption medium. Including washes, an organ may be perfused for up to about 0.75 hours to about 10 hours per gram of solid organ or tissue (generally >50 grams), or about 12 hours to about 72 hours, per gram of tissue (generally <50 grams). Decellularization time is dependent upon the vascular and cellular density of the organ or tissue with limited scaling for overall mass. Therefore, as general guidance the time ranges and masses above are provided. Perfusion generally is adjusted to physiologic conditions including pulsatile flow, rate and pressure.

A decellularized organ or tissue has the extracellular matrix (ECM) component of all or most regions of the organ or tissue, including ECM components of the vascular tree. ECM components can include any or all of the following: fibronectin, fibrillin, laminin, elastin, members of the collagen family (e.g., collagen I, III, and IV), ECM associated growth proteins including growth factors and cytokines, glycosaminoglycans, ground substance, reticular fibers and thrombospondin, which can remain organized as defined structures such as the basal lamina. Successful decellularization is defined as the absence of detectable myofilaments, endothelial cells, smooth muscle cells, and nuclei in histologic sections using standard histological staining procedures or removal of over 97% of detectable DNA as measured by fluorometric assay. Residual cell debris may be removed from the decellularized organ or tissue.

The morphology and the architecture of the ECM is maintained during and following the process of decellularization. "Morphology" as used herein refers to the overall shape of the organ, tissue or of the ECM, while "architecture" as used herein refers to the exterior surface, the interior surface, and the ECM therebetween.

The morphology and architecture of the ECM may be examined visually and/or histologically. For example, the basal lamina on the exterior surface of a solid organ or within the vasculature of an organ or tissue should not be removed or significantly damaged due to perfusion decellularization. In addition, the fibrils of the ECM should be similar to or significantly unchanged from that of an organ or tissue that has not been decellularized.

One or more compounds may be applied in or on a decellularized organ or tissue to, for example, preserve the decellularized organ, or to prepare the decellularized organ or tissue for recellularization and/or to assist or stimulate cells during the recellularization process. Such compounds include, but are not limited to, one or more growth factors (e.g., VEGF, DKK-1, FGF, BMP-1, BMP-4, SDF-1, IGF, HGF, Activin A, Retinoic Acid, and bFGF,), immune modulating agents (e.g., cytokines, glucocorticoids, IL2R antagonist, leucotriene antagonists), chemical (clozapine-N-oxide, phosphoinositide-3-kinase inhibitor, and Nicotinamide) and/or factors that modify the coagulation cascade (e.g., aspirin, heparin-binding proteins, and heparin). In addition, a decellularized organ or tissue may be further treated with, for example, irradiation (e.g., UV, gamma) to reduce or eliminate the presence of any type of microorganism remaining on or in a decellularized organ or tissue.

Exemplary Perfusion Decellularization of Heart
PEG Decellularization Protocol

Hearts are washed in 200 ml PBS containing 100 U/mL penicillin, 0.1 mg/mL Streptomycin, 0.25 µg/mL Amphotericin B, 1000 U of hepatin, and 2 mg of Adenocard with no recirculation. Hearts are then decellularized with 35 ml polyethyleneglycol (PEG; 1 g/mL) for up to 30 minutes with manual recirculation. The organ is then washed with 500 mL PBS for up to 24 hours using a pump for recirculation. The washing step is repeated at least twice for at least 24 hours each time. Hearts are exposed to 35 ml DNase I (70 U/mL) for at least 1 hour with manual recirculation. The organs are washed again with 500 ml PBS for at least 24 hours.

Triton X and Trypsin Decellularization Protocol

Hearts are washed in 200 ml PBS containing 100 U/mL Penicillin, 0.1 mg/mL Streptomycin, 0.25 µg/mL Amphotericin B, 1000 U of hepatin, and 2 mg of Adenocard for at least about 20 minutes with no recirculation. Hearts are then decellularized with 0.05% Trypsin for 30 minutes followed by perfusion with 500 mL PBS containing 5% Triton-X and 0.1% ammonium-hydroxide for about 6 hours. Hearts are perfused with deionized water for about 1 hour, and then perfused with PBS for 12 hours. Hearts are then washed 3 times for 24 hours each time in 500 mL PBS using a pump for recirculation. The hearts are perfused with 35 ml DNase I (70 U/mL) for 1 hour with manual recirculation and washed twice in 500 mL PBS for at least about 24 hours each time using a pump for recirculation.

1% SDS Decellularization Protocol

Hearts are washed in 200 mL PBS containing 100 U/mL Penicillin, 0.1 mg/mL Streptomycin, 0.25 µg/mL Amphotericin B, 1000 U of hepatin, and 2 mg of Adenocard for at least about 20 minutes with no recirculation. The hearts are decellularized with 500 mL water containing 1% SDS for at least about 6 hours using a pump for recirculation. The hearts are then washed with deionized water for about 1 hour and washed with PBS for about 12 hours. The hearts are washed three times with 500 mL PBS for at least about 24 hours each time using a pump for recirculation. The heart is then perfused with 35 ml DNase I (70 U/mL) for about 1 hour using manual recirculation, and washed three times with 500 mL PBS for at least about 24 hours each time using a pump for recirculation.

Triton X Decellularization Protocol

Hearts are washed with 200 mL PBS containing 100 U/mL Penicillin, 0.1 mg/ml Streptomycin, 0.25 µg/mL Amphotericin B, 1000 U of hepatin, and 2 mg of Adenocard (adenosine) for at least about 20 minutes with no recirculation. Hearts are then decellularized with 500 mL water containing 5% Triton X and 0.1% ammonium hydroxide for at least 6 hours using a pump for recirculation. Hearts are then perfused with deionized water for about 1 hour and then with PBS for about 12 hours. Hearts are washed by perfusing with 500 mL PBS 3 times for at least 24 hours each time using a pump for recirculation. Hearts are then perfused with 35 ml DNase I (70 U/mL) for about 1 hour using manual recirculation, and washed three times in 500 ml PBS for about 24 hours each time.

Hearts may be perfused at a coronary perfusion pressure of 60 cm $H_2O$. Although not required, the hearts may be mounted in a decellularization chamber and completely submerged and perfused with PBS containing antibiotics for 72 hours in recirculation mode at a continuous flow of 5 mL/minute to wash out as many cellular components and detergent as possible.

Detection of Decellularization

Successful decellularization may be measured by the lack of nucleic acid in histologic sections. Successful preservation of vascular structures may be assessed by perfusion with 2% Evans Blue prior to embedding tissue sections. Highly efficient decellularization may be observed when an organ is first perfused antegradely with an ionic detergent (1% sodium-dodecyl-sulfate (SDS), approximately 0.03 M) dissolved in deionized $H_2O$ at a constant coronary perfusion pressure and then perfused antegradely with a non-ionic detergent (1% Triton X-100) to remove the SDS and presumably to renature the extracellular matrix (ECM) proteins. Intermittently, the organ may be perfused retrogradely with phosphate buffered solution to clear obstructed capillaries and small vessels.

To demonstrate intact vascular structures following decellularization, a decellularized organ may be stained via Langendorff perfusion with Evans Blue to stain vascular basement membrane and quantify macro- and micro-vascular density. Further, polystyrene particles may be perfused into and through an organ to quantify volume, the level of vessel leakage, and to assess the distribution of perfusion by analyzing effluent and tissue sections. A combination of three criteria are assessed and compared to isolated non-decellularized organ: 1) an even distribution of polystyrene particles, 2) significant change in leakiness at some level 3) microvascular density.

Exemplary Perfusion Decellularization of Liver

For liver isolation, the caval vein is exposed through a median laparotomy, dissected and canulated using a mouse aortic canula (Radnoti Glass, Monrovia, Calif.). The hepatic artery and vein and the bile duct are transsected and the liver was carefully removed from the abdomen and submerged in sterile PBS (Hyclone, Logan, Utah) to minimize pulling force on portal vein. 15 minutes of heparinized PBS perfusion is followed by 2-12 hours of perfusion with 1% SDS (Invitrogen, Carlsbad, Calif.) in deionized water and 15 minutes of 1% Triton-X (Sigma, St. Louis, Mo.) in deionized water. The liver is then continuously perfused with antibiotic containing PBS (100 U/ml penicillin-G (Gibco, Carlsbad, Calif.), 100 U/ml streptomycin (Gibco, Carlsbad, Calif.), 0.25 µg/ml Amphotericin B (Sigma, St. Louis, Mo.)) for 124 hours.

120 minutes of SDS perfusion followed by perfusion with Triton-X 100 are sufficient to generate a completely decellularized liver. Movat pentachrome staining of decellularized liver confirms retention of characteristic hepatic organization with central vein and portal space containing hepatic artery, bile duct and portal vein.

Recellularization of Organs or Tissues

A decellularized organ or tissue is contacted with a population of cells, either differentiated (mature or primary) cells, stem cells, or partially differentiated cells. Thus, the cells can be totipotent cells, pluripotent cells, or multipotent cells, and can be uncommitted or committed, and may be single-lineage cells. The cells may be undifferentiated cells, partially differentiated cells, or fully differentiated cells including fetal derived cells. Cells may include progenitor cells, precursor cells, or "adult" derived stem cells including umbilical cord cells and fetal stem cells. Cells useful in the matrices of the invention include embryonic stem cells (as defined by the National Institute of Health (NIH); see, for example, the Glossary at stemcells.nih.gov on the World Wide Web) and iPS cells.

Examples of cells that can be used to recellularize an organ or tissue include, without limitation, embryonic stem cells, umbilical cord blood cells, tissue-derived stem or progenitor cells, bone marrow-derived step or progenitor cells, blood-derived stem or progenitor cells, mesenchymal stem cells (MSC), skeletal muscle-derived cells, multipotent adult progenitor cells (MAPC), or iPS cells Additional cells that can be used include cardiac stem cells (CSC), multipotent adult cardiac-derived stem cells, cardiac fibroblasts, cardiac microvasculature endothelial cells, aortic endothelial cells, coronary endothelial cells, microvascular endothelial cells, venous endothelial cells, arterial endothelial cells, smooth muscle cells, cardiomyocytes, hepatocytes, beta-cells, keratinocytes, purkinji fibers, neurons, bile duct epithelial call, islet cells, pneumocytes, clara cells, brush boarder cells, or podocytes. Bone marrow-derived stem cells such as bone marrow mononuclear cells (BM-MNC), endothelial or vascular stem or progenitor cells, and peripheral blood-derived stem cells such as endothelial progenitor cells (EPC) may also be used as cells.

The number of cells that are introduced into and onto a perfusion decellularized scaffold may depend both the organ (e.g., which organ, the size and weight of the organ) or tissue and the type and developmental stage of the regenerative cells. Different types of cells may have different tendencies as to the population density those cells will reach. Similarly, different organ or tissues may be cellularized at different densities. By way of example, a decellularized organ or tissue can be "seeded" with at least about 1,000 (e.g., at least 10,000, 100,000, 1,000,000, 10,000,000, or 100,000,000) cells; or can have from about 1,000 cells/mg tissue (wet weight, e.g., prior to decellularization) to about 10,000,000 cells/mg tissue (wet weight) attached thereto.

Cells can be introduced ("seeded") into a decellularized organ or tissue by injection into one or more locations. In addition, more than one type of cell may be introduced into a decellularized organ or tissue. For example, a population of differentiated cell types can be injected at multiple positions in a decellularized organ or tissue or different cell types may be injected into different portions of a decellularized organ or tissue. Alternatively, or in addition to injection, cells or a cocktail of cells may be introduced by perfusion into a cannulated decellularized organ or tissue. For example, cells can be perfused into a decellularized organ using a perfusion medium, which can then be changed to an expansion and/or differentiation medium to induce growth and/or differentiation of the cells. Location specific differentiation may be achieved by placing cells into the various locations within the organ, e.g., into regions of the heart, such as, atrial, ventricular or nodal.

During recellularization, an organ or tissue is maintained under conditions in which at least some of the cells can multiply and/or differentiate within and on the decellularized organ or tissue. Those conditions include, without limitation, the appropriate temperature and/or pressure, electrical and/or mechanical activity, force, the appropriate amounts of $O_2$ and/or $CO_2$, an appropriate amount of humidity, and sterile or near-sterile conditions. During recellularization, the decellularized organ or tissue and the regenerative cells attached thereto are maintained in a suitable environment. For example, the cells may require a nutritional supplement (e.g., nutrients and/or a carbon source such as glucose), exogenous hormones or growth factors, and/or a particular pH.

Cells may be allogeneic to a decellularized organ or tissue (e.g., a human decellularized organ or tissue seeded with human cells), or cells may be xenogeneic to a decellularized organ or tissue (e.g., a pig decellularized organ or tissue seeded with human cells). "Allogeneic" as used herein refers to cells obtained from the same species as that from which the organ or tissue originated (e.g., related or unrelated individuals), while "xenogeneic" as used herein refers to cells obtained from a species different than that from which the organ or tissue originated.

Stem or progenitor media may contain a variety of components including, for example, KODMEM medium (Knockout Dulbecco's Modified Eagle's Medium), DMEM, Ham's F12 medium, FBS (fetal bovine serum), FGF2 (fibroblast growth factor 2), KSR or hLIF (human leukemia inhibitory factor). The cell differentiation media may also contain supplements such as L-Glutamine, NEAA (non-essential amino acids), P/S (penicillin/streptomycin), N2, B27 and beta-mercaptoethanol. It is contemplated that additional factors may be added to the cell differentiation media, including, but not limited to, fibronectin, laminin, heparin, heparin sulfate, retinoic acid, members of the epidermal growth factor family (EGFs), members of the fibroblast growth factor family (FGFs) including FGF2, FGF7, FGF8, and/or FGF10, members of the platelet derived growth factor family (PDGFs), transforming growth factor (TGF)/ bone morphogenetic protein (BMP)/growth and differentiation factor (GDF) factor family antagonists including but not limited to noggin, follistatin, chordin, gremlin, cerberus/ DAN family proteins, ventropin, high dose activin, and amnionless or variants or functional fragments thereof. TGF/BMP/GDF antagonists could also be added in the form of TGF/BMP/GDF receptor-Fc chimeras. Other factors that may be added include molecules that can activate or inactivate signaling through Notch receptor family, including but not limited to proteins of the Delta-like and Jagged families as well as inhibitors of Notch processing or cleavage, or variants or functional fragments thereof. Other growth factors may include members of the insulin like growth factor family (IGF), insulin, the wingless related (WNT) factor family, and the hedgehog factor family or variants or functional fragments thereof. Additional factors may be added to promote mesendoderm stem/progenitor, endoderm stem/ progenitor, mesoderm stem/progenitor, or definitive endoderm stem/progenitor proliferation and survival as well as survival and differentiation of derivatives of these progenitors.

In one embodiment, perfusion decellularized matrices are combined with iPS or ES cells differentiated using the embryoid body (EB) method. For example, human iPS cell lines reprogrammed by transduction, e.g., lentiviral-mediated transduction, of transcription factors (OCT4, SOX2, NANOG and LIN28; Oct3/4, Sox2, Klf4, and c-Myc; or Oct3/4, Sox2, and Klf4) are employed. iPS clones of fetal origin or of newborn origin may be employed. Human ES cell lines may also be employed. iPS cells and ES cells may be maintained on irradiated mouse embryonic fibroblasts (MEFs) at a density of 19,500 cells/cm$^2$ in 6-well culture plates (Nunc) in DMEM/F12 culture medium supplemented with 20% KnockOut serum replacer (Invitrogen), 0.1 mmol/L nonessential amino acids, 1 mmol/L L-glutamine, and 0.1 mmol/L β-mercaptoethanol (Sigma). In addition, the medium may be supplemented with 100 ng/mL, zebrafish basic fibroblast growth factor for iPS cells, and with 4 ng/mL human recombinant basic fibroblast growth factor (Invitrogen) for hES cells. iPS and ES cell lines may also be maintained on gelatinized 100-mm dishes in DMEM (Sigma-Aldrich) containing 15% fetal calf serum (FCS; Sigma-Aldrich), 0.1 µmol/L 2-mercaptoethanol (2ME), and 1,000 units/ml LIF (Chemicon International). For differentiation, these cells may treated with 0.25% Trypsin/ethylenediaminetetraacetic acid (GIBCO), and transferred to gelatinized 6-well plates in α-minimum essential medium (GIBCO) supplemented with 10% FCS and 0.05 µmol/L 2ME, at a concentration of 3×10$^4$ cells/well.

Colonies may be detached from culture plates by incubating with 1 mg/mL dispase (Gibco) solution at 37° C. for 8 to 15 minutes and placed in ultralow attachment plates in suspension culture, e.g., for 4 days. During suspension culture, the medium may be changed at day 1 followed by culture for another 3 days without medium change. EBs are then plated on 0.1% gelatin-coated culture plates, e.g., at the density or 50 to 100 EBs per well, or in the perfusion decellularized ECM and cultured in differentiation medium (e.g., changed daily).

In some instances, an organ or tissue generated by the methods described herein is to be transplanted into a patient. In those cases, the cells used to recellularize a decellularized organ or tissue can be obtained from the patient such that the cells are "autologous" to the patient. Cells from a patient can be obtained from, for example, blood, bone marrow, tissues, or organs at different stages of life (e.g., prenatally, neonatally or perinatally, during adolescence, or as an adult) using methods known in the art. Alternatively, cells used to recellularize a decellularized organ or tissue may be syngeneic (i.e., from an identical twin) to the patient, cells can be human lymphocyte antigen (HLA)-matched cells from, for example, a relative of the patient or an HLA-matched individual unrelated to the patient, or cells can be allogeneic to the patient from, for example, a non-HLA-matched donor.

Irrespective of the source of the cells (e.g., autologous or not), the decellularized solid organ can be autologous, allogeneic or xenogeneic to a patient.

The progress of cells can be monitored during recellularization. For example, the number of cells on or in an organ or tissue can be evaluated by taking a biopsy at one or more time points during recellularization. In addition, the amount of differentiation that cells have undergone can be monitored by determining whether or not various markers are present in a cell or a population of cells. Markers associated with different cells types and different stages of differentiation for those cell types are known in the art, and can be readily detected using antibodies and standard immunoassays. See, for example, Current Protocols in Immunology, 2005, Coligan et al., Eds., John Wiley & Sons, Chapters 3 and 11. Nucleic acid assays as well as morphological and/or histological evaluation can be used to monitor recellularization.

Exemplary Pancreatic Cell Lineage Differentiation

Upon activation of Pdx1 and Ptf1a, the pancreatic fate is induced from endoderm progenitors. Pancreatic progenitors give rise to ductal, acini, and endocrine progenitors (the latter give rise to $\in$ (ghrelin), PP (pancreatic peptide), β, α (glucagon), and δ (somatastatin) secreting cells). Endocrine progenitors are then differentiated (Ngn3, Hnf6 and Haf1) into different hormone-secreting cells, α, β, δ, PP, and $\in$. Key transcription factors involved in different steps of beta-cell formation are Pax4, Arx, Nkx2.2, Nkx6.1, Pdx1 and Mafa.

Human ES are capable of partial differentiation, e.g., into early or fetal pancreatic endoderm or pancreatic epithelium lineages, as characterized by coexpression of PDX1, FOXA2, HNF6 and NKX6-1 by, e.g., day 12, of in vitro differentiation.

To obtain a "substantially closed" vasculature system with respect to an organ means that, upon perfusion with a liquid, the majority of the liquid is contained within the solid organ and does not leak out of the solid organ, assuming the major vessels are cannulated, ligated, or otherwise restricted. Despite having a "substantially closed" vasculature system, many of the organs listed above have defined "entrance" and "exit" vessels which are useful for introducing and moving the liquid throughout the organ during perfusion, cell culture, and transplantation. Functional beta-cells, perfusable pancreatic ECM scaffold are employed to support beta-cell differentiation in a defined 3D culture environment. The perfused decellularized matrix allows for perfusion through intact vascular network whereas other decellularization technologies disrupt the vascular network and extracellular matrix thus not allowing for perfusion.

The beta-cell differentiation protocol may be as described in D'Amour et al, *Nat. Biotech.*, 24:1392 (2006), but with modifications at two of the stages. The first modification eliminates cyclopamine (inhibitor of Hedgehog) and substitutes KGF for FGF10 during stage 2 (days 4-6). The other modification, in stage 3, substitutes Noggin for FGF10. The entire differentiation protocol is as follows. Initiated on days 4-6 after passage (depending on culture density), sequential, daily media changes are made for the entire differentiation protocol. After a brief wash in PBS (with Mg/Ca), the cells are cultured in RPMI (without FBS), activin A (100 ng/ml) and Wnt3a (25 ng/ml) for the first day. The next day the medium is changed to RPMI with 0.2% vol/vol FBS and activin A (100 ng/mL), and the cells are cultured for 2 additional days. Next, the cells are briefly washed with PBS (with Mg/Ca) and then cultured in RPMI with 2% vol/vol FBS and KGF (25-50 ng/mL) for 3 days. The medium is changed to DMEM with 1% vol/vol B27 supplement, KAAD-cyclopamine (0.25 M), all-trans retinoic acid (RA, 2 M) and Noggin (50 ng/mL) for 3 days. The medium is changed to DMEM with 1% vol/vol B27 supplement for 3 days.

Alternatively, human ES cell lines H1 and H9 and mouse embryonic fibroblasts are employed. Human ES cell culture medium includes DMEM/F12 (Invitrogen) with 20% Knockout Serum Replacement (KSR) (Invitrogen) containing 8 ng/mL of bFGF (Invitrogen), Nonessential amino acids (1:100, Invitrogen), 4 mM 1-Glutamine, 0.1 mM 2-Mercaptoethanol (Invitrogen). Penicillin/Streptomycin (1:100, Invitrogen); store at 4° C.

Human ES cell differentiation medium includes (a) Chemical Defined Medium (CDM): 50% IMDM (Invitrogen) plus 50% F12 Nutrient Mixture (Invitrogen), supplemented with Insulin-Transferrin-Selenium-A (1:100, Invitrogen), 450 mM Monothioglycerol (Sigma), and 5 mg/mL Albumin Fraction V (Sigma). (b) Islet Maturation Medium (IMM):DMEM/F12, Insulin-Transferrin-Selenium-A fraction V (Sigma). Factors for human ES cell to insulin-producing cell differentiation are: Activin A (R&D System) 50-100 ng/mL, all-trans Retinoic Acid (Sigma) $10^{-6}$M bFGF (Invitrogen) 10 ng/mL and Nicotinamide (Sigma) 10 mM.

hES cell lines are maintained following a typical protocol. Before induction, hES cells are split, e.g., as 1; 3 (60% confluent), and replated onto tissue culture dishes, e.g., 1% Matrigel-coated tissue culture dishes, or introduced to ECM. hES cells are incubated with hES culture medium overnight for attachment.

Undifferentiated human ES cells are first cultured in CDM containing Activin A for 4 days. Then, the differentiated cells were further induced with RA in CDM for 4 days and transferred from CDM culture medium into DMEM/F12 islet maturation medium with bFGF added as a pancreatic cell maturation factor for 3 days. Finally, the differentiated cells are switched to DMEM/F12 islet maturation medium containing bFGF and nicotinamide for another 5 days. To induce human ES cells to differentiate into definitive endoderm cells, the medium is changed into CDM or DMEM/F12 medium with 50-100 ng/mL Activin A. After a 4-day differentiation, human ES cells are further induced with $10^{-6}$M RA in CDM or DMEM/F12 medium for another 4 days for pancreatic lineage-specific cells. For insulin producing cells, the pancreatic lineage-specific cells are treated with Activin A and RA and then transferred from CDM or DMEM/F12 medium to IMM containing 10 ng/mL bFGF as a pancreatic cell maturation factor for 3 days. The differentiated cells are switched to IMM containing 10 mM Nicotinamide and 10 ng/mL bFGF for another 3-7 days for insulin-producing cell maturation.

Controlled System for Decellularizing and/or Recellularizing an Organ or Tissue

A system (e.g., a bioreactor) for decellularizing and/or recellularizing an organ or tissue generally includes at least one cannulation device for cannulating an organ or tissue, a perfusion apparatus for perfusing the organ or tissue through the cannula(s), and means (e.g., a containment system) to maintain a sterile environment for the organ or tissue. Cannulation and perfusion are well-known techniques in the art. A cannulation device generally includes size-appropriate hollow tubing for introducing into a vessel, duct, and/or cavity of an organ or tissue. Typically, one or more vessels, ducts, and/or cavities are cannulated in an organ. A perfusion apparatus can include a holding container for the liquid (e.g., a cellular disruption medium) and a mechanism for moving the liquid through the organ (e.g., a pump, air pressure, gravity) via the one or more cannulae. The sterility of an organ or tissue during decellularization and/or recellularization can be maintained using a variety of techniques known in the art such as controlling and filtering the air flow and/or perfusing with, for example, antibiotics, anti-fungals or other anti-microbials to prevent the growth of unwanted microorganisms.

A system to decellularize and recellularize organ or tissues as described herein can possess the ability to monitor certain perfusion characteristics (e.g., pressure, volume, flow pattern, temperature, gases, pH), mechanical forces (e.g., ventricular wall motion and stress), and electrical stimulation (e.g., pacing). As the coronary vascular bed changes over the course of decellularization and recellularization (e.g., vascular resistance, volume), a pressure-regulated perfusion apparatus is advantageous to avoid large fluctuations. The effectiveness of perfusion can be evaluated in the effluent and in tissue sections. Perfusion volume, flow pattern, temperature, partial $O_2$ and $CO_2$ pressures and pH can be monitored using standard methods.

Sensors can be used to monitor the system (e.g., bioreactor) and/or the organ or tissue. Sonomicrometry, micromanometry, and/or conductance measurements can be used to acquire pressure-volume or preload recruitable stroke work information relative to myocardial wall motion and performance. For example, sensors can be used to monitor the pressure of a liquid moving through a cannulated organ or tissue; the ambient temperature in the system and/or the temperature of the organ or tissue; the pH and/or the rate of flow of a liquid moving through the cannulated organ or tissue; and/or the biological activity of a recellularizing organ or tissue. In addition to having sensors for monitoring such features, a system for decellularizing and/or recellularizing an organ or tissue also can include means for maintaining or adjusting such features. Means for maintaining or adjusting such features can include components such as a thermometer, a thermostat, electrodes, pressure sensors, overflow valves, valves for changing the rate of flow of a liquid, valves for opening and closing fluid connections to solutions used for changing the pH of a solution, a balloon, an external pacemaker, and/or a compliance chamber. To help ensure stable conditions (e.g., temperature), the chambers, reservoirs and tubings can be water-jacketed.

A system for generating an organ or tissue may be controlled by a computer-readable storage medium in combination with a programmable processor (e.g., a computer-readable storage medium as used herein has instructions stored thereon for causing a programmable processor to perform particular steps). For example, such a storage medium, in combination with a programmable processor, may receive and process information from one or more of the sensors. Such a storage medium in conjunction with a programmable processor also can transmit information and instructions back to the bioreactor and/or the organ or tissue.

An organ or tissue undergoing recellularization may be monitored for biological activity. The biological activity can be that of the organ or tissue itself such as for cardiac tissue, electrical activity, mechanical activity, mechanical pressure, contractility, and/or wall stress of the organ or tissue. In addition, the biological activity of the cells attached to the organ or tissue may be monitored, for example, for ion transport/exchange activity, cell division, and/or cell viability. See, for example, Laboratory Textbook of Anatomy and Physiology (2001, Wood, Prentice Hall) and Current Protocols in Cell Biology (2001, Bonifacino et al., Eds, John Wiley & Sons). As discussed above, it may be useful to simulate an active load on an organ during recellularization. A computer-readable storage medium of the invention, in combination with a programmable processor, may be used to coordinate the components necessary to monitor and maintain an active load on an organ or tissue.

In one embodiment, the weight of an organ or tissue may be entered into a computer-readable storage medium as described herein, which, in combination with a programmable processor, can calculate exposure times and perfusion pressures for that particular organ or tissue. Such a storage medium may record preload and afterload (the pressure before and after perfusion, respectively) and the rate of flow. In this embodiment, for example, a computer-readable storage medium in combination with a programmable processor can adjust the perfusion pressure, the direction of perfusion, and/or the type of perfusion solution via one or more pumps and/or valve controls.

The invention will be further described in the following examples, which do not limit the scope of the invention described in the claims.

Example 1

Comparison of Perfusion Vs Immersion

Figure 1A:
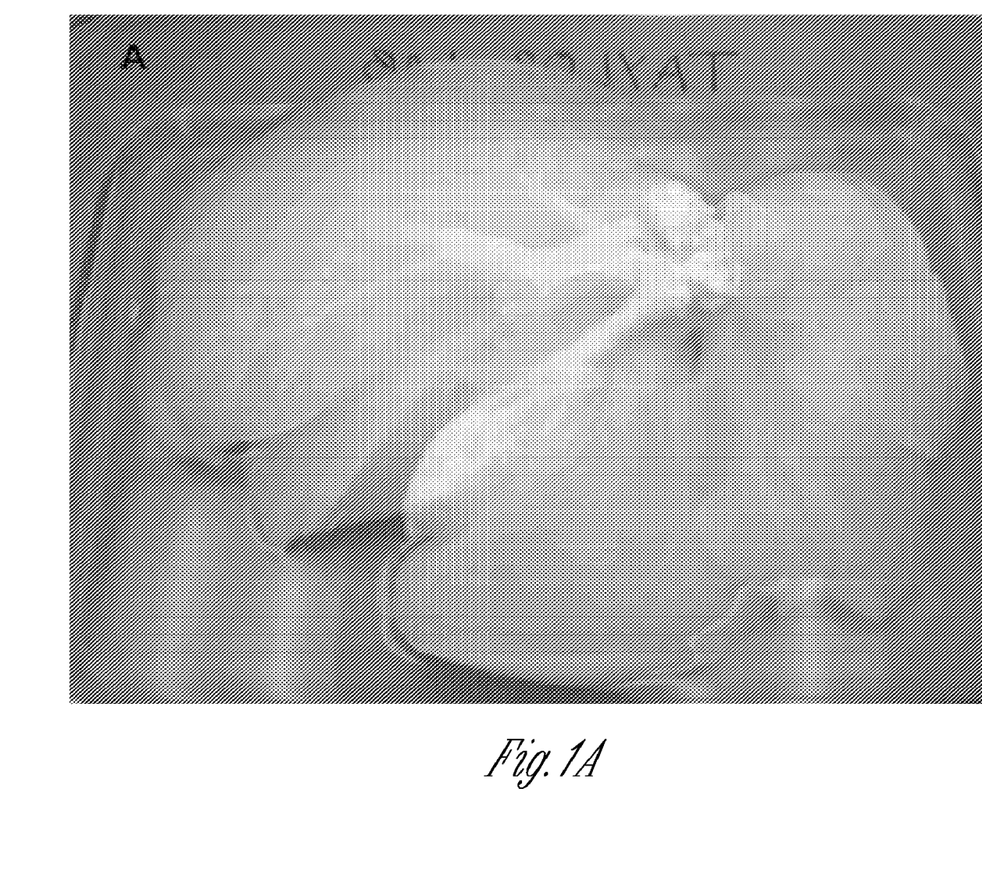
FIG. 1A shows a photograph of a porcine liver that was perfusion decellularized.
Figure 1B:
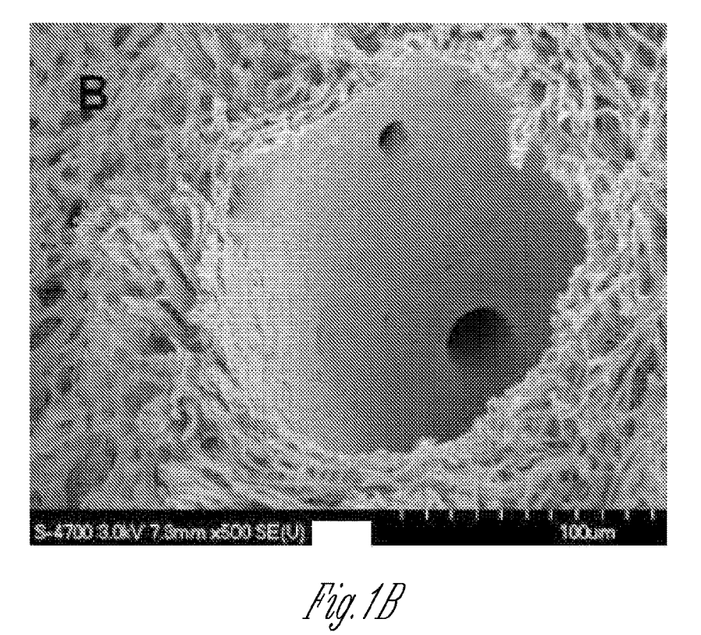
FIGS. 1B-C show a scanning electron microscope (SEM) photograph of a vessel and the parenchymal matrix, respectively, of the perfusion decellularized porcine liver.
Figure 1C:
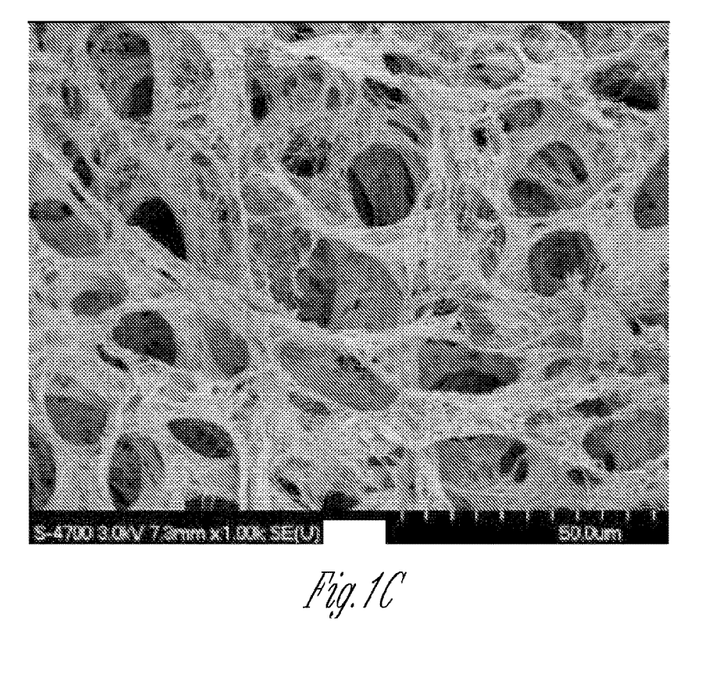
Figure 2:
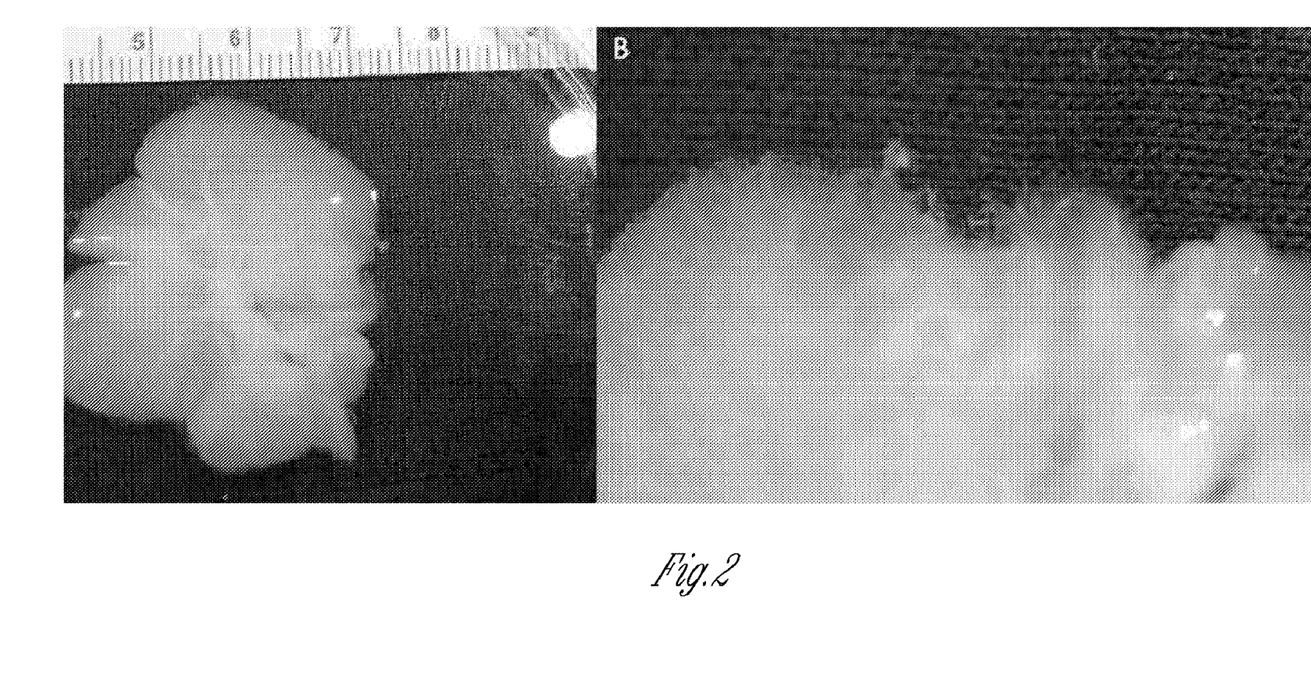
FIG. 2 provides a gross view of an immersion decellularized rat liver, in which fraying of the matrix can be seen at both low (left) and high (right) magnification.

FIG. 1A shows a photograph of a porcine liver that was perfusion decellularized, and FIGS. 1B and 1C show SEM of a vessel and the parenchymal matrix, respectively, of the perfusion decellularized porcine liver. These photographs show the vascular conduits and the matrix integrity of a perfusion decellularized organ. On the other hand, FIG. 2 shows a gross view of an immersion decellularized rat liver, in which fraying of the matrix can be seen at both low (left) and high (right) magnification.

Figure 3:
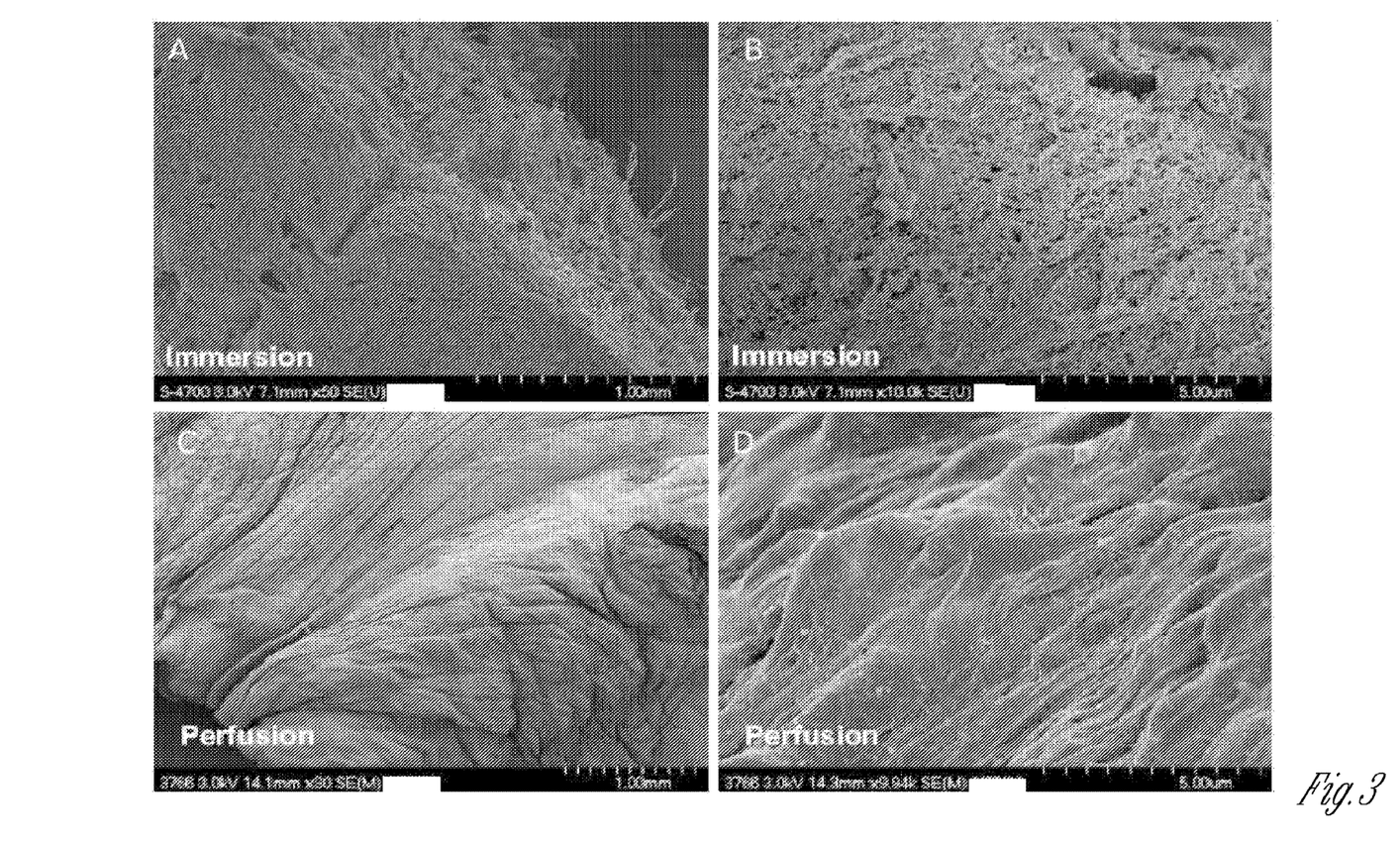
FIG. 3 shows SEM photographs of immersion decellularized rat liver (A and B) and perfusion decellularized rat liver (C and D).
Figure 4:
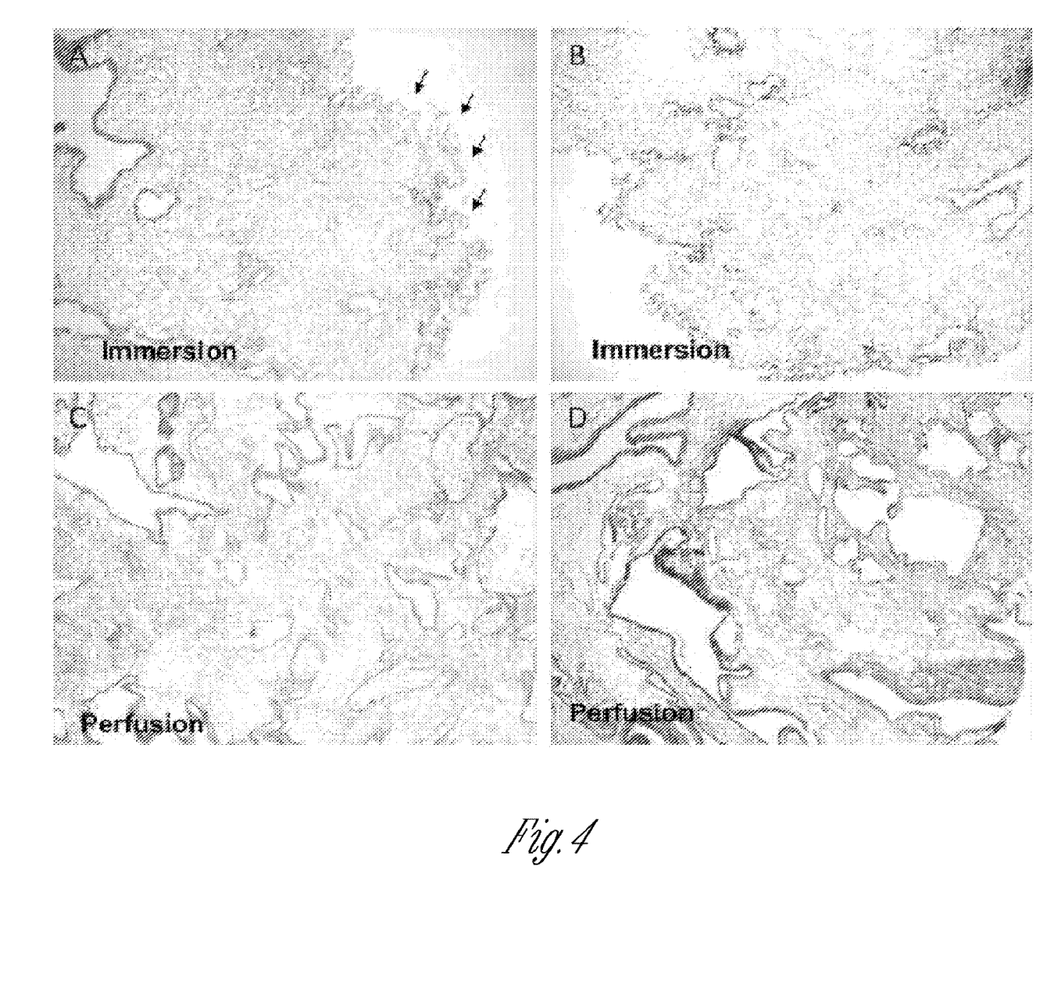
FIG. 4 provides histology of immersion decellularized liver (A, H&E staining; B, Trichrome staining) and perfusion decellularized liver (C, H&E staining; D, Trichrome staining)

FIG. 3 shows SEM of immersion decellularized rat liver (A and B) and perfusion decellularized rat liver (C and D). These results clearly indicate that immersion decellularization significantly compromised the organ capsule (Glisson's capsule), while perfusion decellularization retained the capsule. In addition, FIG. 4 shows histology of immersion decellularized liver (A, H&E staining; B, Trichrome staining) and perfusion decellularized liver (C, H&E staining; D, Trichrome staining). The immersion decellularized rat liver did not retain cells or dye upon injection.

Example 2

Islet cells have been transplanted into the liver or kidney via the portal vein or under the capsule, respectively, to provide a vascularized bed for the islet cells. However, the removal of those cells, for instance, after they cease to produce insulin or are the subject of rejection, is not feasible. The advantages of preparing the grafts described herein include, but are not limited to, easy removal of the graft, the graft may be prepared ex vivo, allowing for characterization of the graft pre-implantation, and the use of various stem cells and cell culture media conditions that can be used to further drive differentiation and/or maturation to achieve a desired outcome (function).

A perfusion decellularized liver, liver lobe or portion thereof may be employed to deliver and maintain islet cells and/or beta cells in vivo. For example, a perfusion decellularized liver, liver lobe or portion thereof is re-endothelialized before or after injection of islet cells or islet like cells, where islet like cells express early islet related markers but are not fully functional and require additional maturation including regenerative cells with the potential to become an insulin responsive cell including islet cells, islet like cells, beta cell, beta cell like or insulin like cell beta-cells etc. Seeding may be accomplished via injection, perfusion, or a combination thereof. Insulin producing cells may be encapsulated, for example but not limited to in alginate, biocompatible nanocoatings, PEG, polysulphone, polyvinyl alcohol, low molecular weight dextran sulfate, chemical modified polymers for surface modification, or photopolymers, to avoid immune rejection upon transplantation with the re-endothelialized liver graft providing immediate vascular support for survival. Any type of endothelial cell may be employed and the resulting graft transplanted into the host. Moreover, the seeding can be accomplished before or after transplantation. A revascularized liver graft provides a well vascularized environment for the islet cells, beta cells or islet like cells, thereby providing vascular support, and allows for insulin regulation.

For re-endothelialization, in one embodiment, endothelial cells and endothelial progenitor cells are obtained by culturing embryonic stem cells (ESCs) or induced pluripotent stem cells (iPSCs) under appropriate conditions to direct the stem cells down an endothelial lineage. Endothelial progenitor cells are cells that have begun to differentiate into endothelial cells or have the potential to (e.g., multi-potent; e.g., lineage-restricted; e.g., cells that are destined to become endothelial cells) but are not considered fully differentiated endothelial cells. For example, endothelial cells typically express platelet endothelial cell-adhesion molecule-1 (PE-CAM1; aka CD31) and may also express one or more of the following markers: VEGFR-1 (aka Flt-1), VEGFR-2 (aka Flk-1), guanylate-binding protein-1 (GBP-1), thrombomodulin (aka CD141), VE-cadherin (aka CD144), von Willebrand factor (vWF), and intercellular adhesion molecule 2 (ICAM-2). Generally, endothelial progenitor cells also are able to take up acetylated LDL, and, further, may migrate toward VEGF and/or form tubes on a Matrigel.

ESCs or iPSCs can be further cultured under conditions that result in fully differentiated endothelial cells. Additionally or alternatively, endothelial cells can be obtained from any number of sources such as blood, skin, liver, heart, lung, retina, and any other tissue or organ that harbors endothelial cells. For example, representative endothelial cells include, without limitation, blood endothelial cells, bone marrow endothelial cells, circulating endothelial cells, human aorta endothelial cells, human brain microvascular endothelial cells, human dermal microvascular endothelial cells, human intestinal microvascular endothelial cells, human lung microvascular endothelial cells, human microvascular endothelial cells, hepatic sinusoidal endothelial cells, human saphenous vein endothelial cells, human umbilical vein endothelial cells, lymphatic endothelial cells, microvessel endothelial cells, microvascular endothelial cells, pulmonary artery endothelial cells, retinal capillary endothelial cells, retinal microvascular endothelial cells, vascular endothelial cells, umbilical cord blood endothelial cells, and combinations thereof. As those of skill in the art would understand, this is not intended to be an exhaustive list of endothelial cells.

Endothelial cells can be obtained, for example, from one of the many depositories of biological material around the world. See, for example, the American Type Culture Collection (ATCC.org on the World Wide Web) or the International Depositary Authority of Canada (IDAC; nml-lnm.gc.ca on the World Wide Web). Endothelial cells or endothelial progenitor cells also can be obtained from the individual that will be the recipient of the transplanted tissue or organ matrix. These cells would be considered to be autologous to the recipient. Additionally, under certain circumstances, the relationship between the tissue or organ matrix and the endothelial cells or endothelial progenitor cells can be allogeneic (i.e., different individuals from the same species); in other instances, the relationship between the tissue or organ matrix and the endothelial cells or endothelial progenitor cells can be xenogeneic (i.e., individuals from different species).

A composition that includes endothelial cells or endothelial progenitor cells typically is delivered to a tissue or organ matrix in a solution that is compatible with the cells (e.g., in a physiological composition) under physiological conditions (e.g., 37° C.). A physiological composition, as referred to herein, can include, without limitation, buffers, nutrients (e.g., sugars, carbohydrates), enzymes, expansion and/or differentiation medium, cytokines, antibodies, repressors, growth factors, salt solutions, or serum-derived proteins. As used herein, a composition that "consists essentially of" endothelial cells or endothelial progenitor cells is a composition that is substantially free of cells other than endothelial cells or endothelial progenitor cells but may still include any of the components that might be found in a physiological composition (e.g., buffers, nutrients, etc.).

Endothelial cells or endothelial progenitor cells may be introduced into an organ or tissue matrix by perfusion. As described in WO 2007/025233, perfusion occurs via the vasculature or vasculature-type structure of the organ or tissue matrix. Perfusion to re-endothelialize an organ or tissue matrix should be at a flow rate that is sufficient to circulate the physiological composition of cells through the vasculature; however, perfusion to re-endothelialize a tissue or organ matrix typically is performed under little to no pressure (e.g., less pressure than is used in the pre-cellular perfusion step to expand and flush the vascular bed). Perfusion with the endothelial cells or endothelial progenitor cells can be multi-directional (e.g., antegrade and retrograde) to even further optimize re-endothelialization.

The number of endothelial cells or endothelial progenitor cells that is introduced into the vasculature of a tissue or organ matrix for re-endothelialization is dependent on both the organ or tissue (e.g., which organ or tissue, the size and weight of the organ or tissue, the developmental stage of the organ or tissue, and/or the extent of vascularization of the organ or tissue) and the type and developmental stage of the endothelial cells or endothelial progenitor cells. In addition, more than one type of endothelial cell or endothelial progenitor cell (e.g., a cocktail of endothelial cells or endothelial progenitor cells) can be introduced into the vasculature of an organ or tissue matrix.

Endothelial cells can be seeded at known or estimated density, or seeded at a lower density and allowed to proliferate in vitro or in vivo to reach a confluent level. Different types of endothelial cells or endothelial progenitor cells may have different tendencies as to the population density those cells will reach, and, similarly, different organ or tissue matrices may be re-endothelialized at different densities. Simply by way of example, at least about 100 (e.g., at least about $10^3$, $10^4$, $10^5$, $10^6$, $10^7$, $10^9$ or $10^{10}$) endothelial cells or endothelial progenitor cells, or stem cells, can be introduced into an organ or tissue matrix.

Other cell types may be introduced to the extracellular matrix along with the endothelial cells or islet cells, e.g., mesenchymal stem cells (MSC) may be helpful with stabilizing the matrix for endothelial cells or for the sensitization of seeded islet cells into the patient to avoid immune rejection of unprotected islet or beta cells.

To determine whether a re-endothelialized graft has obtained a sufficient population of endothelial cells, endothelial cell density may be measured by monitoring the cell culture media after a specified time for the consumption or accumulation of amino acids, key water-soluble vitamins, glucose/lactose, and trace elements.

Islet and/or beta cells or stem or progenitor cells may be injected and/or perfused into a completely re-endothelialized liver graft. Re-endothelialization following islet or beta cell introduction into the decellularized matrix may be accomplished either through the perfusion or injection of endothelial cells into the matrix, e.g., vasculature matrix, followed by a defined culturing time, where the proliferation rate, growth rate, or density of endothelial cells may be monitored to determine when the graft is ready for implantation.

To introduce islet cells or beta cells into a re-endothelialized graft, the cells are injected or perfused into the liver graft while it is being continuously perfused at a pressure that provides a sufficient concentration of nutrients to the injected cells. For in vivo introduction of islet or beta cells to a mammal, a mammal may receive at least 10,000 islet "equivalents" per kilogram of body weight.

To determine the functionality of the seeded islet cells or beta cells in a mammal engrafted with the cells described above or a graft produced ex vivo as described above, overall insulin production in response to a glucose challenge is measured. In addition, C-peptide and urea production may be measured as a function of the islet cells or beta cells within the graft.

The graft may be transplanted anywhere in the body, e.g., for a liver graft with the hepatic or portal vein being anastomosed to an arterial supply and either the resulting hepatic or portal vein being anastomosed to a vein. Alternatively, the hepatic artery could be anastomosed to an arterial supply and the hepatic and portal vein anastomosed to a vein. In one embodiment, the graft is anastomosed to a liver.

In one embodiment, a perfusion decellularized liver, liver lobe or portion thereof is re-endothelialized ex vivo, for example, via injection or perfusion, for about 1 to 6 weeks, before ex vivo injection or perfusion of islet cells, beta cells or islet like cells into the matrix, for about 1 to 2 weeks, and the resulting graft implanted into a host mammal. Other cells, e.g., mesenchymal stem cells, may be included with cells employed to re-endothelialize the decellularized liver, liver lobe or portion thereof, or included with the islet cells, beta cells or islet like cells, or provide immune sensitization to the transplanted host. In one embodiment, a perfusion decellularized liver, liver lobe or portion thereof is re-endothelialized ex vivo before implantation and in vivo injection of islet cells, beta cells or islet like cells into the implanted re-endothelialized graft. In one embodiment, a perfusion decellularized liver, liver lobe or portion thereof is implanted into a host, the graft is then re-endothelialized and after about 1 to 6 weeks, islet cells, beta cells or islet like cells are injected or perfused into the revascularized graft. The graft is tested for insulin production, e.g., ex vivo or in vivo, from about 1 to 2 weeks after islet cells, beta cells or insulin like cells are introduced to the graft.

In one embodiment, islet cells, beta cells or islet like cells are introduced ex vivo to a perfusion decellularized liver, liver lobe or portion thereof, for example, via injection or perfusion, before ex vivo injection or perfusion of endothelial cells, and the resulting recellularized and re-endothelialized graft implanted into a host mammal. In one embodiment, islet cells, beta cells or islet like cells are introduced ex vivo to a perfusion decellularized liver, liver lobe or portion thereof, for example, via injection or perfusion, before implantation and subsequent in vivo injection or perfusion of endothelial cells into the graft. In one embodiment, a perfusion decellularized liver, liver lobe or portion thereof is implanted into a host, the graft is then implanted with islet cells, beta cells or islet like cells and then endothelial cells, e.g., via injection or perfusion.

After introduction of islet cells, beta cells, insulin like cells or cells that are capable of differentiating into those cells into the matrix, the graft may be tested for insulin, amylin, glucagon, somatostatin, pancreatic polypeptide and/or ghrelin production, e.g., ex vivo or in vivo.

In one embodiment, cells may be seeded using the decellularized vasculature extracellular matrix. For instance, the hepatic artery or vein or both may be employed to introduce cells to a perfusion decellularized liver.

The resulting re-endothelialized insulin producing graft may allow for control of blood glucose in mammals having an insulin deficiency, e.g., as a result of an autoimmune disease such as Type I diabetes or Type II diabetes where there is a relative insufficiency of insulin.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method to prepare a graft comprising:
providing a perfusion decellularized extracellular matrix of a mammalian liver, a portion of a liver, a liver lobe or a portion thereof that is >8 cm$^3$, and two populations of cells, wherein the two populations of cells comprise a first population of mammalian cells comprising endothelial cells, stem cells capable of differentiation into endothelial cells, progenitor cells capable of differentiation into endothelial cells, or any combination thereof, and a second population of mammalian cells comprising insulin producing cells, stem cells capable of differentiation into insulin producing cells, progenitor cells capable of differentiation into insulin producing cells, or any combination thereof; and
contacting the perfusion decellularized extracellular matrix and the two populations of cells under conditions and for a period of time so that cells in the first population re-endothelialize a vasculature of the perfusion decellularized extracellular matrix and cells in the second population recellularize the perfusion decellularized extracellular matrix, wherein if the cells in the first population are stem cells or progenitor cells, the conditions allow for those cells to differentiate into endothelial cells, and wherein if the cells in the second population are stem cells or progenitor cells, the conditions allow for those cells to differentiate into insulin producing cells.

2. The method of claim 1 wherein the perfusion decellularized extracellular matrix is a portion >8 cm$^3$ of a perfusion decellularized extracellular matrix of a liver or a liver lobe.

3. The method of claim 1 wherein the cells in the first population, the second population, or both, are allogeneic or xenogeneic to the decellularized extracellular matrix.

4. The method of claim 1 wherein the cells in the first population, the second population, or both, comprise iPS cells, human embryonic stem cells, primary cells, or a combination thereof.

5. The method of claim 1 wherein the perfusion decellularized extracellular matrix comprises an intact vascular network.

6. The method of claim 1 wherein the conditions comprise perfusing the extracellular matrix with media.

7. The method of claim 6 wherein the media comprises an activator or inhibitor of a differentiation pathway selected to provide for cell-specific differentiation wherein the activator or inhibitor is selected from the group consisting of Activin A, Retinoic Acid, bFGF, clozapine-N-oxide, phosphoinositide-3-kinase inhibitor, Nicotinamide, and combinations thereof.

8. The method of claim 1 wherein the first population, the second population, or both, is contacted with the extracellular matrix by injection, perfusion, or a combination thereof.

9. The method of claim 1 wherein the second population comprises a plurality of different cell types.

10. The method of claim 1 wherein the second population of mammalian cells is encapsulated prior to the contacting.

11. The method of claim 1 wherein the extracellular matrix is from a nonhuman mammal and the cells in the first population, the second population, or both, are human cells.

12. The method of claim 1 further comprising implanting the extracellular matrix in a mammal.

13. The method of claim 12 wherein the extracellular matrix is implanted in the mammal prior to contact with the first population, the second population, or both.

14. The method of claim 13 wherein the cells in the first population, the second population, or both, are injected into the mammal.

15. The method of claim 12 wherein the extracellular matrix is implanted in the mammal after contact with the first population, but before contact with the second population.

16. The method of claim 12 wherein the extracellular matrix is implanted in the mammal after contact with the second population but before contact with the first population.

17. The method of claim 12 wherein the extracellular matrix is implanted in the mammal after contact with the first population and the second population.

18. The method of claim 12 wherein the mammal is a human.

19. The method of claim 1 wherein the graft produces insulin.

20. The method of claim 1 wherein the insulin producing cells comprise islet cells, beta cells, or a combination thereof.

21. The method of claim 1 wherein the cells in the first population, the second population, or both, are autologous to a human in need of the extracellular matrix.

22. The method of claim 1 wherein the mammalian liver, portion of the liver, liver lobe or portion thereof is from a pig.

23. The method of claim 1 wherein the mammalian liver, portion of the liver, liver lobe or portion thereof comprises a vascular system.

24. The method of claim 23 wherein the vascular system is substantially closed.

\* \* \* \* \*

UNITED STATES PATENT AND TRADEMARK OFFICE
CERTIFICATE OF CORRECTION

| | |
|---|---|
| PATENT NO. | : 10,213,525 B2 |
| APPLICATION NO. | : 14/777360 |
| DATED | : February 26, 2019 |
| INVENTOR(S) | : Jeffrey Ross |

Page 1 of 1

It is certified that error appears in the above-identified patent and that said Letters Patent is hereby corrected as shown below:

On the Title Page

Item (73) "Assignee", in Column 1, Line 1, delete "Micromatrix" and insert --Miromatrix-- therefor Signed and Sealed this
Twelfth Day of December, 2023

Katherine Kelly Vidal
*Director of the United States Patent and Trademark Office*